(12) United States Patent
Lim

(10) Patent No.: US 7,711,429 B1
(45) Date of Patent: May 4, 2010

(54) METHODS AND SYSTEMS FOR CONNECTING ELECTRICAL LEADS TO AN IMPLANTABLE MEDICAL DEVICE

(75) Inventor: Wisit Lim, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 381 days.

(21) Appl. No.: 11/767,322

(22) Filed: Jun. 22, 2007

(51) Int. Cl.
*A61N 1/05* (2006.01)

(52) U.S. Cl. .............................. 607/37; 607/36; 439/11; 439/13; 439/43; 439/53; 439/151; 439/620.01; 439/909; 439/924.1; 600/377; 600/386; 600/481

(58) Field of Classification Search ............... 439/11, 439/13, 43, 53, 151–153, 620.01, 909, 924.1; 600/372–373, 377, 386, 481, 529, 544, 546; 607/36–38
See application file for complete search history.

(56) References Cited

U.S. PATENT DOCUMENTS

| | | | |
|---|---|---|---|
| 4,860,750 A | 8/1989 | Frey et al. |
| 5,000,705 A | 3/1991 | Kinka et al. |
| 5,261,395 A | 11/1993 | Oleen et al. |
| 5,413,595 A | 5/1995 | Stutz, Jr. |
| 5,489,225 A | 2/1996 | Julian |
| 5,545,188 A | 8/1996 | Bradshaw et al. |
| 5,766,042 A | 6/1998 | Ries et al. |
| 5,951,595 A | 9/1999 | Moberg et al. |
| 6,192,277 B1 | 2/2001 | Lim et al. |
| 6,339,190 B1 | 1/2002 | Chung |
| 6,428,368 B1 | 8/2002 | Hawkins et al. |
| 6,609,029 B1 | 8/2003 | Mann et al. |
| 6,984,145 B1 | 1/2006 | Lim |

FOREIGN PATENT DOCUMENTS

WO 9510324 4/1995

OTHER PUBLICATIONS

NonFinal Office Action, mailed Mar. 28, 2005: Related U.S. Appl. No. 10/826,656.
Notice of Allowance, mailed May 18, 2005: Related U.S. Appl. No. 10/826,656.
Supplemental Notice of Allowability, mailed Aug. 2, 2005: Related U.S. Appl. No. 10/826,656.

*Primary Examiner*—Carl H Layno
*Assistant Examiner*—Deborah Malamud

(57) ABSTRACT

Methods, lead retention assemblies and systems may provide a secure connection of electrical leads to an implantable medical device, such as a pacemaker or a defibrillator. The method may include: providing a lead retention assembly including a support member, a first side clamp and a second side clamp, a first port and a second port each defining a respective receptacle in conjunction with the support, and a fastener configured to urge both the first and second side clamps toward the support upon actuation of the fastener; providing at least two electrical lead bodies each including a respective proximal end portion; inserting the respective proximal end portions into the respective receptacles to be in electrical communication with a respective electrical contact in the respective receptacles; and actuating the fastener to thereby clamp the proximal end portions of the respective electrical lead bodies within the first and second ports.

17 Claims, 13 Drawing Sheets

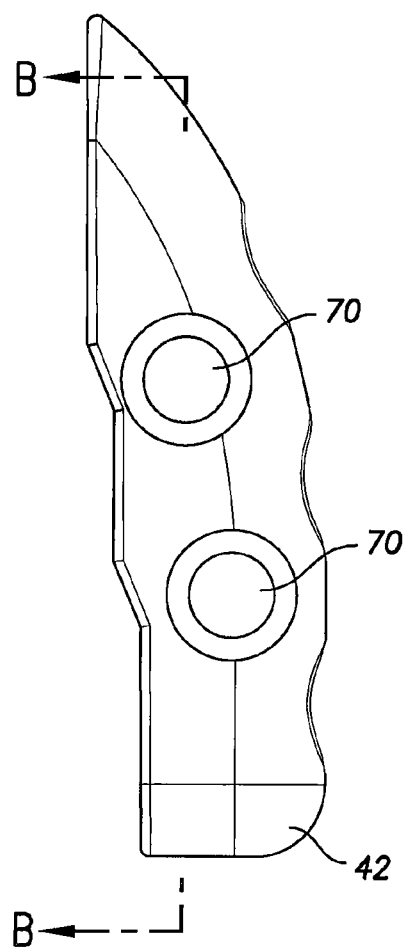
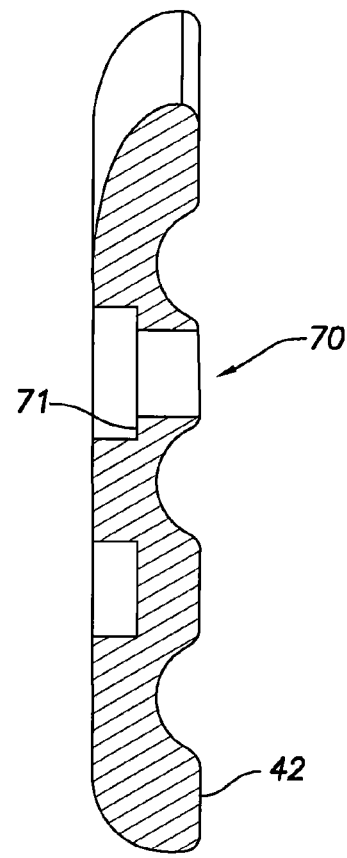

METHODS AND SYSTEMS FOR CONNECTING ELECTRICAL LEADS TO AN IMPLANTABLE MEDICAL DEVICE

FIELD OF THE INVENTION

The present invention relates generally to lead retention assemblies of implantable medical devices and methods for connecting implantable medical leads to such devices. More particularly, the present invention relates to methods and mechanisms for securely locking implantable medical leads within a lead retention assembly.

BACKGROUND OF THE INVENTION

Cardiac pacemakers, and other implantable stimulation devices such as cardioverters and defibrillators, are typically hermetically sealed within a housing or casing (sometimes also referred to as a "can") to isolate the electronic circuits contained within the device from the body environment. Such devices require that electrical signals be reliably passed between the hermetically sealed circuitry and external connectors without compromising the hermeticity of the device. Depending on the configuration of the implantable device there may be multiple electrical paths required between the device and its external connectors for delivering, for example, multi-chamber or multi-site stimulation and shock therapy, and for receiving sensed cardiac signals. These paths should be electrically and mechanically integrated with the device to provide a safe, long-term lead retention assembly that does not compromise the hermetic package.

Typically, a hermetic housing feedthrough electrically couples the electronic circuits contained within the device housing to the lead retention assembly. The feedthrough may extend through the wall of the hermetically sealed casing into the lead retention assembly so as to couple the electronic circuits within the casing to lead-receiving receptacles within the lead retention assembly. Each lead has one or more electrical terminals on a proximal end thereof, typically in the form of a pin terminal and one or more conductive ring terminals. Typically, the pin is electrically coupled to a distal tip electrode and is therefore sometimes called the "tip terminal." When the proximal end of the lead is inserted into the lead receptacle of a lead retention assembly, contacts within the receptacle come into contact with corresponding terminals on the lead so as to couple the lead to the electronic circuits within the implantable stimulation device via the feedthrough assembly. Needless to say, a completely dependable electrical connection is useful between the lead terminals and the corresponding lead retention assembly contacts. At the same time, the lead retention assembly being capable of releasing the lead from the lead receptacle during explantation or other subsequent surgical procedure may be useful, as may doing so while remaining tightly sealed against the entry of body fluids.

It is known in prior art lead retention assemblies to electrically and mechanically connect the proximal end of the lead within a receptacle of the lead retention assembly by a variety of expedients including captive fastening screw/collet arrangements and setscrews. In such prior art lead retention assemblies in which the lead is fixed within the lead receptacle using a setscrew, the setscrew is often threaded into an electrical connector block within the lead retention assembly. When the screw is advanced, it comes into contact with an associated terminal on the proximal end of the lead, mechanically and electrically coupling the lead and the lead retention assembly.

U.S. Pat. No. 6,984,145, issued Jan. 10, 2006, the entirety of which is incorporated herein by reference, discloses an example of a lead retention assembly mounted on an implantable cardiac stimulation device having a side-actuated mechanism for fixing and tightly sealing electrical leads inserted into lead receptacles.

SUMMARY

There is a need in the art for improved systems and methods for connecting a plurality of electrical leads to an implantable medical device. Although technology related to connection assemblies has advanced to provide various approaches, such approaches tend to be complex and/or expensive. Accordingly, it would be desirable to provide a lead retention assembly for connecting a plurality of electrical leads to an implantable medical device that is more reliable and easier to use.

Various embodiments of the present invention may provide a lead retention assembly in which a fastener is configured to urge both a first side clamp and a second side clamp toward a support upon actuation of the fastener. Such an approach may reduce a number of fasteners needed to secure a plurality of electrical leads.

Some embodiments may provide a lead retention assembly in which the various components are held together in an unclamped state. Such an approach may prevent a loss of parts, and may also facilitate clamping actuation of the lead retention assembly.

Embodiments of the present invention may provide a lead retention assembly for connecting a plurality of electrical leads to an implantable medical device. The lead retention assembly may include at least two receptacles each configured to receive a proximal end portion of a respective electrical lead. Each receptacle may include an electrical contact for electrically connecting the respective electrical lead to electrical circuitry of an implantable medical device. The lead retention assembly may further include a support member, a first side clamp configured to define a first port in conjunction with the support, a second side clamp configured to define a second port in conjunction with the support and a fastener configured to urge both the first and second side clamps toward the support upon actuation of the fastener. Such urging may cause the lead retention assembly to clamp the proximal end portions of the respective electrical leads within the first and second ports.

Embodiments of the present invention may provide a system for connecting electrical leads in an implantable medical device. The system may include an implantable medical device including electrical circuitry and a lead retention assembly configured to be secured to the implantable medical device. The lead retention assembly may include a support member, a first side clamp and a second side clamp. The first and second side clamps may respectively be configured to define first and second ports in conjunction with the support, which ports may include respective receptacles configured to receive a respective electrical lead body. Each receptacle may include an electrical contact for electrically connecting the respective electrical lead body to the electrical circuitry of the implantable medical device. The lead retention assembly may further include a fastener configured to urge both the first and second side clamps toward the support upon actuation of the fastener, to thereby clamp the respective electrical lead bodies within the first and second ports. The system may also include at least two electrical leads each including a proximal end portion configured to be secured in the first and second ports respectively when the first and second side clamps are urged toward the support upon actuation of the fastener.

Embodiments of the present invention may provide a method for connecting electrical leads in an implantable medical device. The method may include providing a lead retention assembly, or system, such as described above; inserting at least two electrical lead bodies, each including a respective proximal end portion, into the respective receptacles to be in electrical communication with a respective electrical contact in the respective receptacles; and actuating the fastener to thereby clamp the proximal end portions of the respective electrical lead bodies within the first and second ports.

Disclosed herein is an implantable pulse generator such as a pacemaker, defibrillator or implantable cardioverter defibrillator (ICD). The generator is configured to have at least first and second implantable cardiac electrotherapy leads secured thereto. In one embodiment, the generator includes a first clamp, a second clamp and an actuator. The first clamp is configured to secure the first lead to the generator. The second clamp is configured to secure the second lead to the generator. The actuator is configured to cause both clamps to secure their respective leads.

Disclosed herein is an implantable pulse generator such as a pacemaker, defibrillator or ICD. The generator is configured to have at least first and second implantable cardiac electrotherapy leads secured thereto. In one embodiment, the generator includes a pair of opposed clamps, a support positioned between the clamps, and an actuator. Rotation of at least a portion of the actuator relative to the support causes both clamps to generally simultaneously increasingly clamp the leads against the front support portion.

Disclosed herein is an implantable pulse generator such as a pacemaker, defibrillator or ICD. The generator is configured to have at least first and second implantable cardiac electrotherapy leads secured thereto. In one embodiment, the generator includes a pair of opposed clamps, a support positioned between the clamps, and a means for generally simultaneously impacting the positional relationship of both clamps relative to the front support portion to secure the leads between the clamps and the support.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 4 is a side elevation view of one of the side clamps of the lead retention assembly of FIG. 2.

FIG. 5 is a cross-sectional view of the side clamp of FIG. 4, taken along line B-B in FIG. 4.

DETAILED DESCRIPTION

The following description is of embodiments presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Although it should be understood that the present invention is applicable to a variety of implantable medical devices, the description herein is principally in the context of a specific example of such devices, namely, an implantable cardiac device, such as a pacemaker and/or defibrillator. However, such description is for the sake of understanding only, and is not limiting.

The disclosed devices, systems and associated methods are directed at connecting a plurality of electrical leads to an implantable medical device. Such connection may occur, for example, before or during implantation of the device, or after the device has been implanted, for example, to replace one or more leads. Although the methods contemplated are described in conjunction with the devices and systems illustrated herein, it should be understood that numerous variations exist for implementing the methods.

Figure 1:
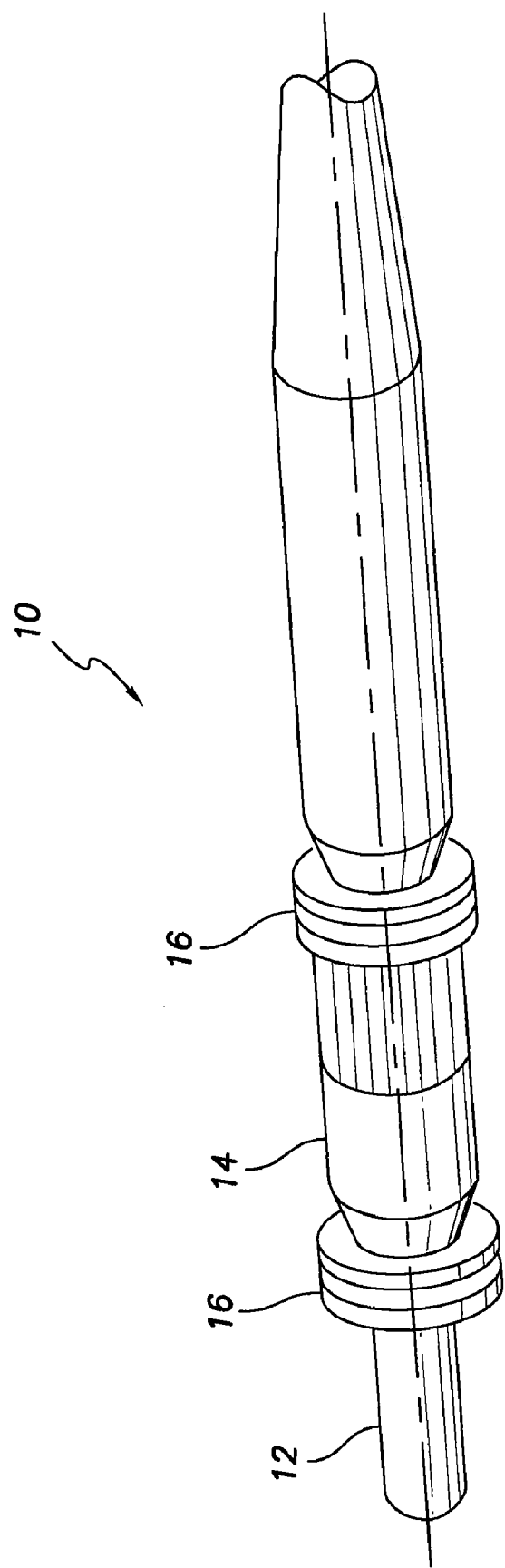
FIG. 1 is a perspective view of the proximal end portion or connective end of a known bipolar lead.

FIG. 1 shows a proximal end portion or connective end 10 of a conventional transvenous, bipolar pacing lead. The proximal lead end portion 10 may be configured to be secured to an implantable medical device using a lead retention assembly as described further below. In particular, the proximal lead end portion 10 may include a pair of coaxial spaced-apart terminals including a tip terminal 12 and a ring terminal 14. The proximal lead end portion 10 may include one or more features 16 that are configured to be engaged by a lead retention assembly.

Such a lead is well known, as is described in the incorporated U.S. Pat. No. 6,984,145. Thus, further details are not discussed. It should be understood that the pacing lead is only an example of an electrical lead that may be used with the devices, systems and methods described herein. In particular, it should be understood that the proximal lead end portion of the electrical lead may or may not include any suitable feature(s) for cooperating with the lead retention assembly, to provide a mechanical engagement and/or a friction fit, as appropriate or desired.

Figure 2:
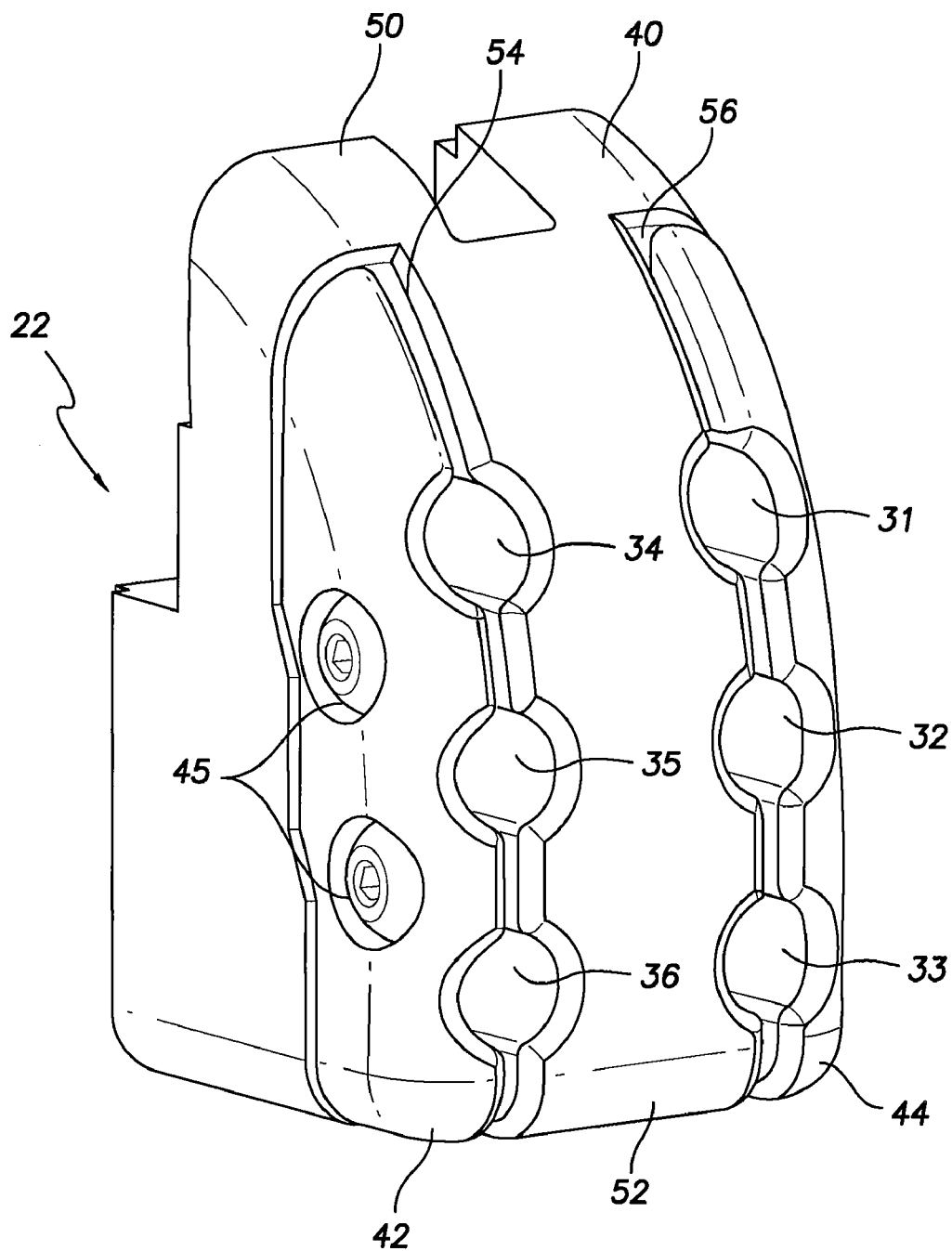
FIG. 2 is a perspective view of an example of a lead retention assembly.

FIG. 2 is a perspective view of an example of a lead retention assembly 22. The lead retention assembly 22 may include a plurality of ports that define a first set of receptacles 31, 32, 33 and a second set of receptacles 34, 35, 36. Each of the receptacles 31-36 may be configured to receive the proximal or connective ends 10 of electrical leads. Six total receptacles are shown to illustrate various details. However, it should be understood that any desired number of receptacles may be used. The bores of the receptacles may include various features suitable for engaging and retaining respective electrical leads, in conjunction with the lead retention assembly 22, as described herein. Further, one or more electrical contacts may be disposed in the bores of the receptacles to provide a connection to electrical circuitry of the implantable medical device to which the lead retention assembly 22 is to be attached.

The lead retention assembly 22 may include a support 40, opposed first and second side clamps 42, 44, and one or more fasteners 45 for securing the side clamps to the support 40 to clamp the connective ends 10 of the leads in place. The support 40 may be molded of a material such as polysulfone or tecothane. The side clamps 42, 44 may be molded of material such as polysulfone or delrin or machined from a material such as titanium or stainless steel. The support 40 may include a rear portion 50 and a nose or front portion 52 that is narrower than the rear portion and defines opposed side recesses 54, 56 for receiving the side clamps 42, 44, respectively. The rear support portion 50, the front support portion 52 and the side clamps 42, 44 include curved outer surfaces that form a substantially continuous, smooth, outer lead retention assembly surface when the side clamps are in their fully clamped position, as illustrated in FIG. 2, for example.

Figure 3:
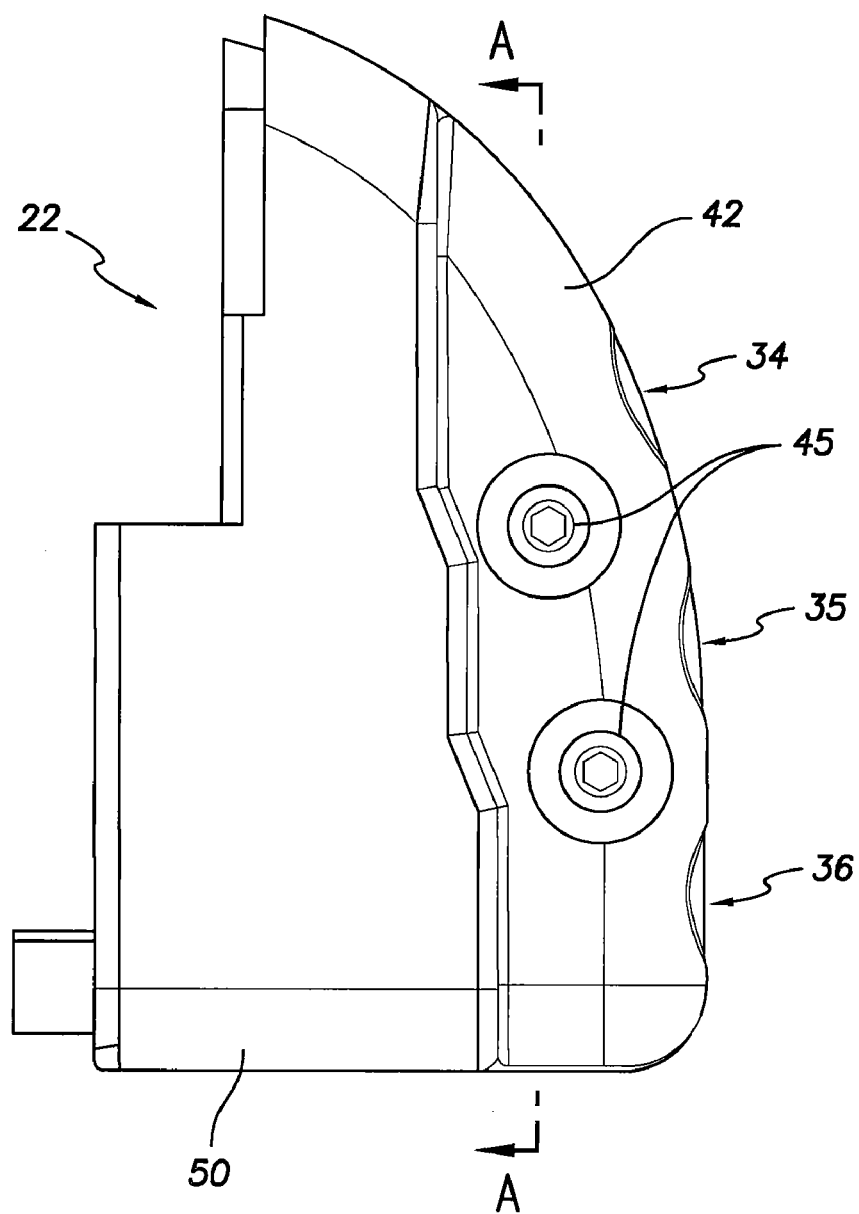
FIG. 3 is a side elevation view of the lead retention assembly depicted in FIG. 2.

FIG. 3 is a side elevation view of the lead retention assembly 22. FIG. 4 is a similar view of the first side clamp 42 removed from the lead retention assembly 22. As shown in the cross-sectional view of the first side clamp 42 in FIG. 5, and with further reference to FIGS. 6-9, a bore 70 for receiving each fastener 45 may extend through the side clamps 42, 44 and the front support portion 52 of the lead retention assembly 22.

Depending on the embodiment, the lead retention assembly 22 may have one, two or more bores 70 and one, two or more fasteners 45. For example, as can be understood from FIGS. 2-8, in one embodiment, the lead retention assembly 22 may have two bores 70 with a fastener 45 within each bore 70. While the various cross-sectional views in the figures are such that only a single one of the multiple bores 70 and fasteners 45 are portrayed in full cross-section, it should be understood that, in at least one embodiment, the configurations of all bores 70 and fasteners 45 of the lead retention assembly 22 are generally identical. Thus, the bore and fastener configurations depicted in FIGS. 5 and 7-11, can be considered to apply equally to all bores 70 and fasteners 45 of an embodiment of the lead retention assembly 22 employing more than one bore 70 and fastener 45. Depending on the embodiment, the statements in this paragraph are also similarly applicable to the embodiments depicted in FIGS. 12-16.

As illustrated in FIGS. 4-9, the bores 70 may include various diameters, threads or other features for cooperating with the fasteners 45. As shown in FIG. 5, the portion of the bore 70 extending through the first side clamp 42 may provide a first outer shoulder 71.

Figure 6:
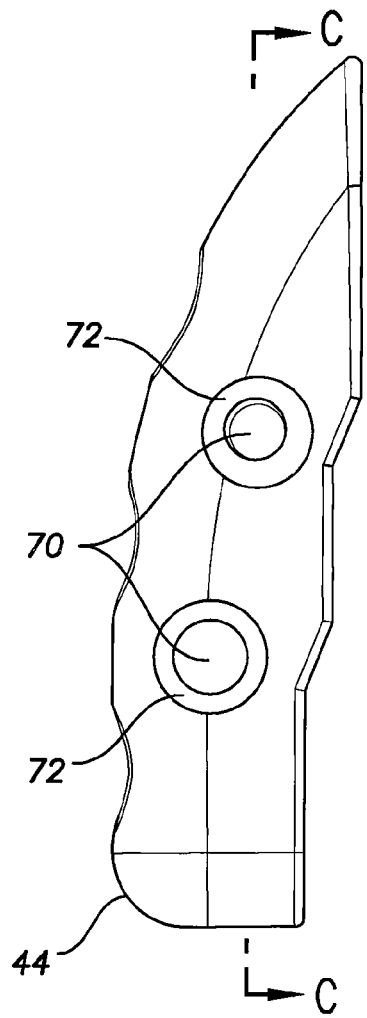
FIG. 6 is a side elevation view of the other one of the side clamps of the lead retention assembly of FIG. 2.
Figure 7:
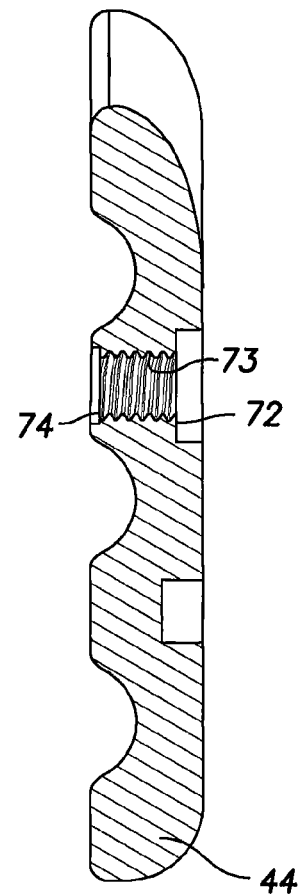
FIG. 7 is a cross-sectional view of the side clamp of FIG. 6, taken along line C-C in FIG. 6.

FIG. 6 is a side elevation view of the second side clamp 44. As shown in the corresponding cross-sectional view of the second side clamp 44 in FIG. 7, the portion of the bore 70 extending through the second side clamp 44 may provide a second outer shoulder 72. The portion of the bore 70 extending through the second side clamp 44 may further provide an internal clamp thread 73 and a first inner shoulder 74.

Figure 8:
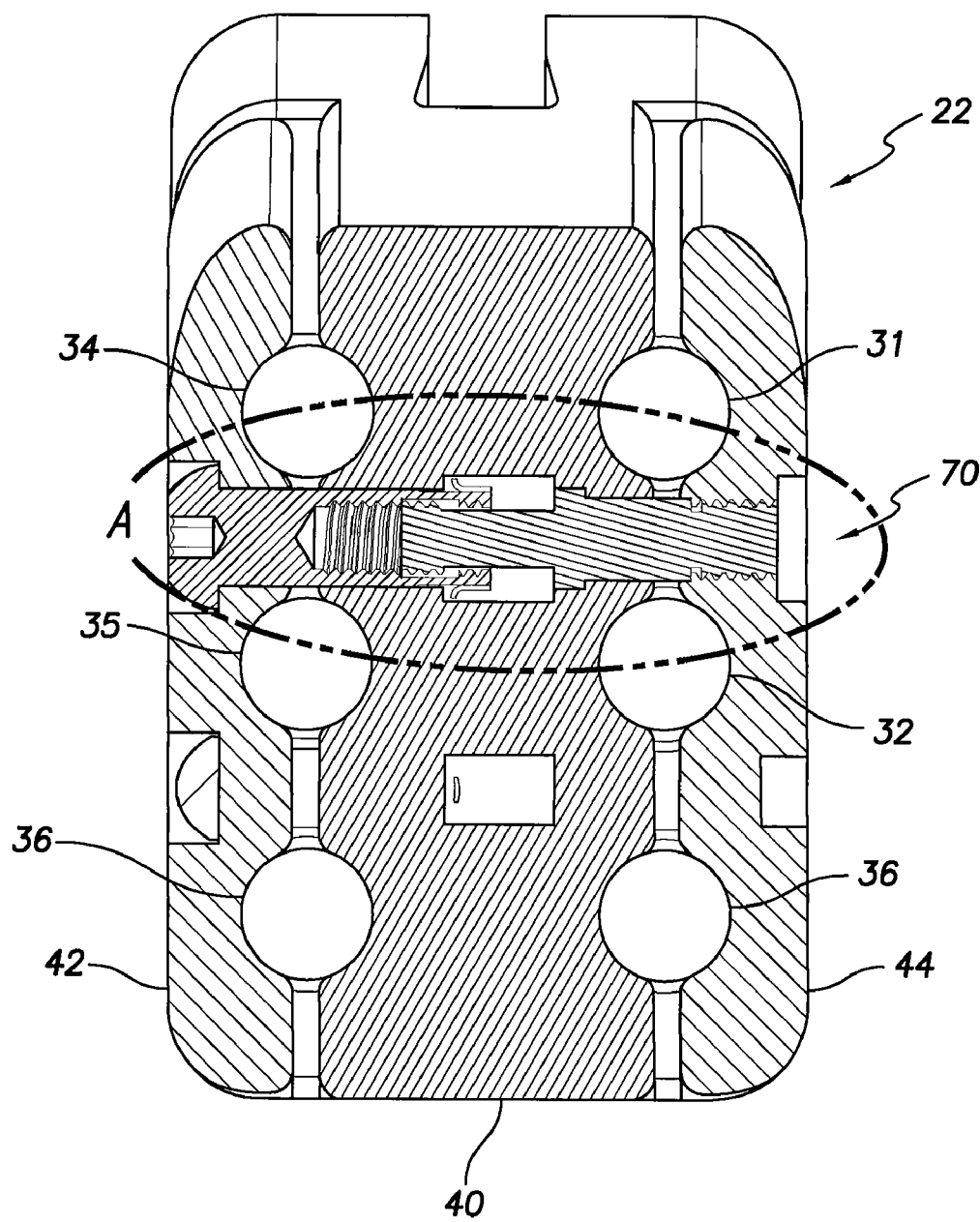
FIG. 8 is a cross sectional view of the lead retention assembly of FIG. 3, taken along line A-A in FIG. 3.
Figure 9:
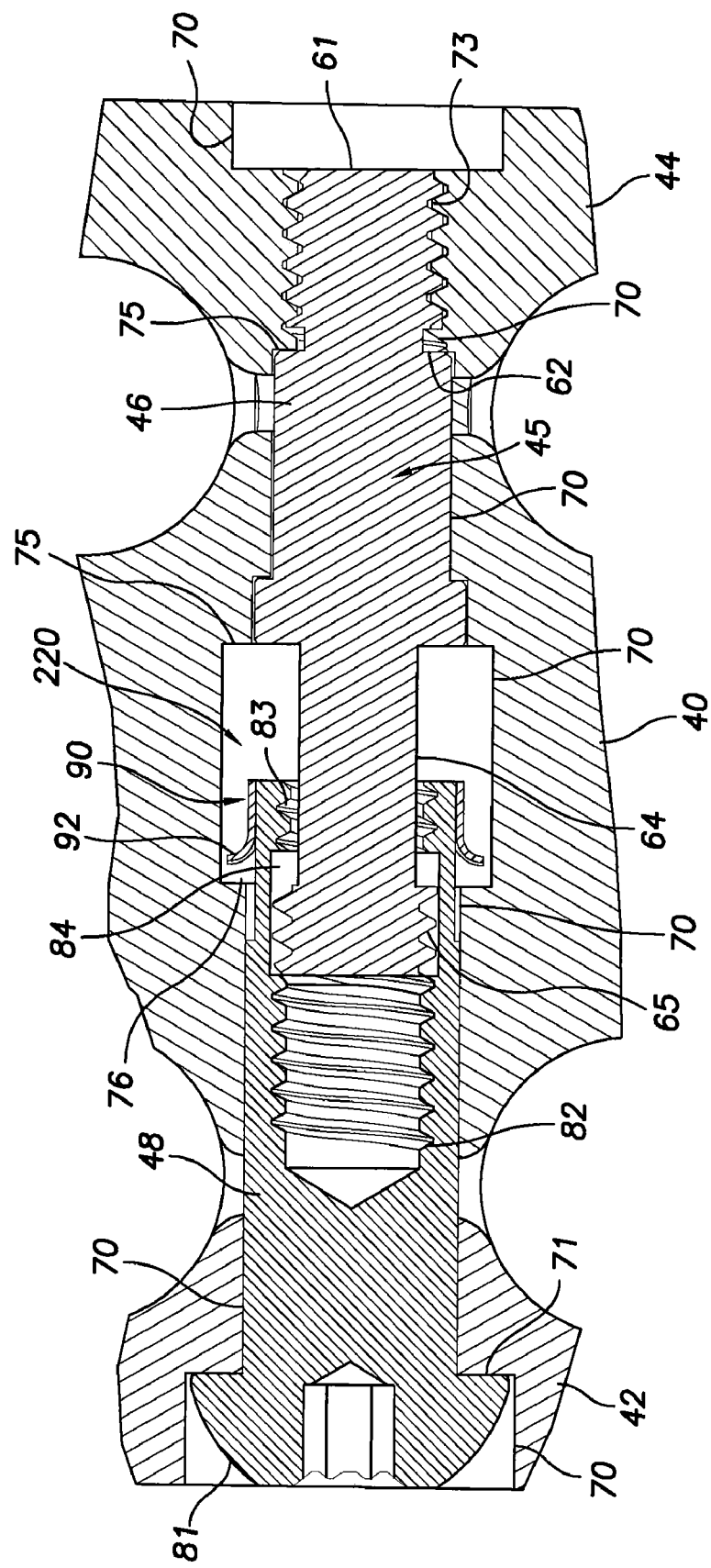
FIG. 9 is a partial enlarged view of detail A in FIG. 8.

As shown in FIG. 8, and in detail in FIG. 9, the portion of the bore 70 extending through the front support portion 52 may provide additional features in the front support portion 52. In particular, the portion of the bore 70 extending through the front support portion 52 may define a second inner shoulder 75, a third inner shoulder 76, and a cavity 220. The fastener 45 may include corresponding features that cooperate with the features of the bore 70, as described below.

Figure 10:
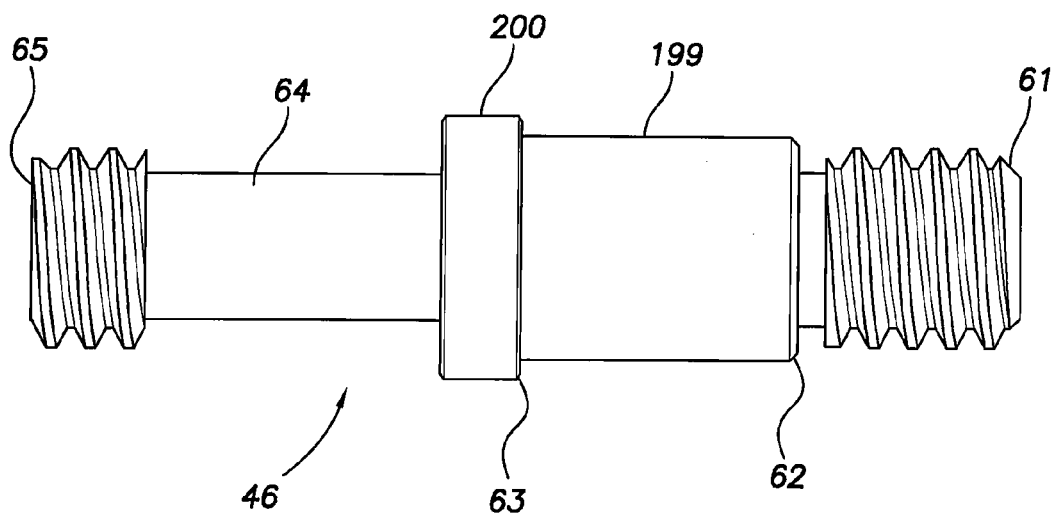
FIG. 10 is a side elevation view of one portion of the fastener of FIG. 8.
Figure 11:
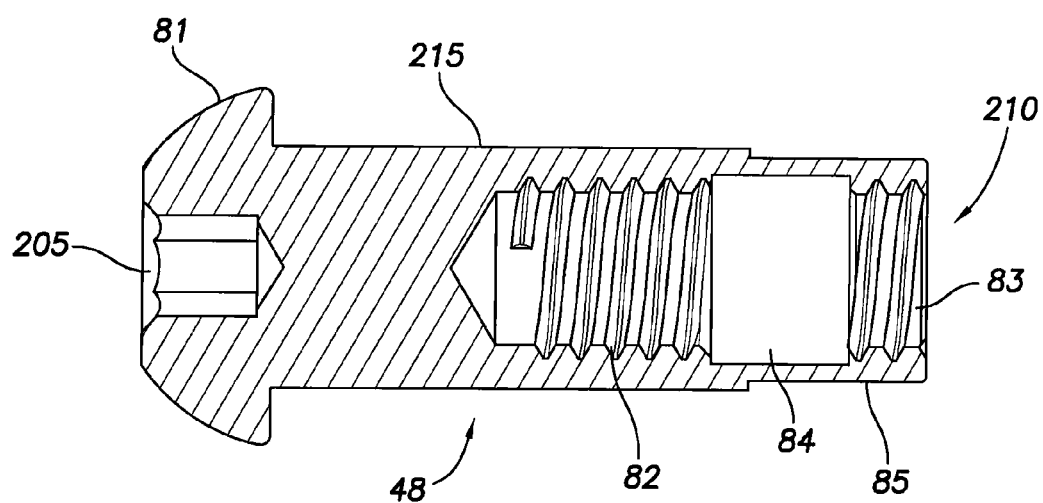
FIG. 11 is a cross-sectional view of the other portion of the fastener of FIG. 8.

The fastener 45 may include a first or male fastener portion 46 and a second or female fastener portion 48. FIG. 10 shows details of the male fastener portion 46. FIG. 11 shows details of the female fastener portion 48. FIGS. 8 and 9 show the male and female fastener portions 46, 48 engaged to render the fastener 45 operative in the lead retention assembly 22 such that a portion of the male fastener portion 46 is received in a portion of the female fastener portion 48.

With reference to FIG. 10, the male fastener portion 46 may include a wide diameter shaft section 199, a narrow diameter shaft section 64, and a ridge or ring 200 located between the two shaft sections. In one embodiment, the ring 200 extends circumferentially about shaft of the male fastener portion 46.

A free end of the wide diameter shaft section 199 of the male fastener portion 46 may include a first threaded end 61 configured to engage the internal clamp thread 73 in the second side clamp 44. The male fastener portion 46 may include a first shoulder 62 between the first threaded end 61 and the ring 200. The first shoulder 62 of the male fastener portion 46 may be configured to abut the first inner shoulder 74 in the second side clamp 44, for example, when the first threaded end 61 of the male fastener portion 46 is fully engaged in the internal clamp thread 73 of the second side clamp 44.

The ring 200 of the male fastener portion 46 may form a second shoulder 63 configured to abut the second inner shoulder 75 in the front support portion 52, for example, when the lead retention assembly 22 is fully opened to the maximum extent, as depicted in FIG. 9 for one embodiment.

The narrow diameter shaft section 64 of the male fastener portion 46 may extend from the ring 200. The free end of the narrow diameter shaft section 64 may include a second threaded end 65. As described below and depicted in FIG. 9, the narrow diameter shaft section 64 may be configured to allow the second threaded end 65 of the male fastener portion 46 to cooperate with the female fastener portion 48.

With reference to FIG. 11, the female fastener portion 48 may include a head 81 configured to engage the first outer shoulder 71 of the first side clamp 42, as depicted in FIG. 9. The head 81 and shoulder 71 engage when the lead retention assembly 22 is fully closed (clamped). Also, the head 81 engages the shoulder 71 so the head 81 can drive the first side clamp 42 towards the front support portion 52 when the first side clamp 42 is being moved towards the fully clamped state.

As indicated in FIG. 11, the head 81 also includes a tool engagement feature 205 for engagably receiving a screwdriver, wrench, etc. Thus, a tool can be used to cause the female fastener portion 48 to rotate within the bore 70 and relative to the male fastener portion 46, thereby causing the male fastener portion 46 to be threadably received within the female fastener portion 48, as indicated in FIG. 9.

As shown in FIG. 11, the female fastener portion 48 may include a cavity or bore 210 extending axially into the female fastener portion 48. The bore 210 may include a first internal thread 82 and a second internal thread 83 longitudinally separated by an unthreaded or threadless portion 84.

As can be understood from FIG. 9, the male and female fastener portions 46, 48 may be secured together by threading the second threaded end 65 of the male fastener portion 46 into the second internal thread 83 of the female fastener portion 48. By threading past the second internal thread 83, the second threaded end 65 of the male fastener portion 46 may be movable within the unthreaded portion 84 of the female fastener portion 48, for example, to provide a limited amount of play or relative movement of the male and female fastener portions 46, 48 while connected. This amount of play or relative movement of the male and female fastener portions 46, 48 provides the side clamps 42, 44 with sufficient play relative to the front support portion 52 to accommodate a lead connective end 10 without having to rotate the female fastener portion 48 within the bore 70.

As illustrated in FIG. 11, the female fastener portion 48 may optionally include a full diameter shaft section 215 and a reduced diameter shaft section 85. The reduced diameter shaft section 85 of the female fastener portion 48 may facilitate connecting an anchor 90 to the female fastener portion 48, as shown in FIGS. 8 and 9. The anchor 90 may be made of nitinol, for example, and may be fixedly attached to the female fastener portion 48, for example, by welding. It should be understood that any other suitable metal or non-metal material may be used for the anchor 90 and that the anchor 90 may be attached in any suitable manner, such as with a mechanical or frictional engagement, or with adhesive.

The anchor 90 may include one or more outwardly extending flange 92. The outwardly extending flange 92 may be of any suitable shape and/or size, as may the anchor 90. For example, the anchor 90 and/or the outwardly extending flange 92 may be annular. Alternatively, the outwardly extending flange 92 may include one or more protrusions or tabs.

As shown in FIG. 9, the outwardly extending flange 92 may be configured to retain the female fastener portion 48 in the cavity 220 inside the support 40 by cooperating with the third inner shoulder 76. Thus, the first side clamp 42, the front support portion and the female fastener portion 48 may be held together, with a suitable amount of play to allow insertion of electrical leads into the lead retention assembly 22. Further, the outwardly extending flange 92 of the anchor 90 may be configured to abut the third inner shoulder 76 on the front support portion 52, for example, when the lead retention assembly 22 is fully opened to the maximum extent.

As can be understood from FIGS. 8 and 9, the second shoulder 63 of the male fastener portion 46 encountering the front support portion 52, specifically, the second inner shoulder 75, prevents the second side clamp 44 from overly moving away from the front support portion 52, thereby preventing the male fastener portion 46 from exiting the bore 70 on the side of the front support portion 52 having the second side clamp 44. Similarly, the flange 92 encountering the front support portion 52, specifically, the third inner shoulder 76, prevents the first side clamp 42 from overly moving away from the front support portion 52, thereby preventing the female fastener portion 48 from exiting the bore 70 on the side of the front support portion 52 having the first side clamp 42.

As discussed above and can be understood from FIG. 9, the male fastener portion 46 may be secured to the second side clamp 44. In one embodiment, this may occur after the male fastener portion 46 is inserted through the bore 70 of the front support portion 52 from the side of the first clamp 42. The large diameter shaft sections 199, 215 of the fastener portions 46, 48 may have generally the same diameter, which is less than the diameter of the bore 70. As a result, the fastener portions 46, 48 can be passed into the bore 70 by entering the bore from the side of the front support portion 52 having the first side clamp 42. The male fastener portion 46 is entered into the bore 70 first with the first threaded end 61 of the male fastener portion 46 leading. The second shoulder 63 of the male fastener portion 46 encountering the second inner shoulder 75 in the front support portion 52 prevents the male fastener portion 46 from overly extending through the bore 70.

In one embodiment, as can be understood from FIG. 9, the female fastener portion 48, with the anchor 90 mounted thereon, is passed anchor end first through the bores 70 of the first side clamp 42 and the front support portion 52. As the anchor 90 passes through the bores 70, the flanges 92 deflect against the sides of the reduced diameter portion 85 of the shaft of the female fastener portion 48, thereby providing sufficient clearance for the anchor end of the female fastener portion 48 to extend through the bores 70. When the flanges 92 clear the third inner shoulder 76 of the front support portion 52 as the anchor end of the female fastener portion 48 enters the cavity 220 of the front support portion 52, the flanges 92 bias outwardly to engage the third inner shoulder 76 and prevent the withdrawal of the female fastener portion 48 from the front support portion 52.

As indicated in FIG. 9, in one embodiment, the first threaded end 61 of the male fastener portion 46 is threaded into the internal clamp thread 73 of the second side clamp 44. Thus, the male fastener portion 46, the second side clamp 44 and the front support portion 52 may be held together, with a suitable amount of play to allow insertion of lead connector ends 10 into the lead retention assembly 22.

In another embodiment, the male fastener portion 46 does not have the first threaded end 61. Instead, the region of male fastener portion 46 having the first threaded end 61 depicted in FIG. 10 is without threads. This threadless area of the male fastener portion 46 is affixed to the hole 73 in the second side clamp 44, the hole 73 being threadless in this embodiment. In one embodiment, the fixation between the male fastener portion 46 and the hole 73 is via adhesive or mechanical or friction fit.

As shown in FIG. 9, the head 81 of the female fastener portion 48 engages the first outer shoulder 71 of the first side clamp 42, and the flange 92 on the shaft of the female fastener portion 48 engages the third inner shoulder 76 of the front support portion 52. As a result, the first side clamp 42, the front support portion 52 and the female fastener portion 48 may be held together, with a suitable amount of play to allow insertion of lead connector ends 10 into the lead retention assembly 22.

As indicated in FIG. 9, in one embodiment, the fastener portions 46, 48 are engaged with each other with the second threaded end 65 of the male fastener portion 46 being received in the bore 210 of the female fastener portion 48. Specifically, a tool is utilized to rotate the female fastener portion 48 in a first direction relative to the male fastener portion 46 such that the second threaded end 65 of the male fastener portion 46 threadably engages the second internal thread 83 of the female fastener portion 48. Further rotation of the female fastener portion 48 in the first direction causes the second threaded end 65 of the male fastener portion 46 to extend deeper into the bore 210 of the female fastener portion 48 until the second threaded end 65 enters the threadless region 84 of the bore 210 of the female fastener portion 48. At this point, the first and second side clamps 42, 44 are secured to the front support portion 52 in such a manner that there is a suitable amount of play between the front support portion 52 and the side clamps 42, 44 to allow insertion of lead connective ends 10 into the lead retention assembly 22.

In one embodiment and as can be understood from FIGS. 2, 8 and 9, subsequent to the insertion of lead connective ends 10 into the appropriate receptacles 31-36, the side clamps 42, 44 are pressed towards the front support portion 52 to cause the second threaded end 65 of the male fastener portion 46 to move across the threadless region 84 of the bore 210 of the female fastener portion 48 to be able to threadably engage the first internal thread 82 of the female fastener portion 48. Further rotation of the female fastener portion 48 in the first direction causes the second threaded end 65 of the male fastener portion 46 to threadably engage and travel along the first internal thread 82 of the female fastener portion 46. As a result, both fastener portions 46, 48 converge inwardly towards the cavity 220, drawing the side clamps 42, 44 towards the front support portion 52 and clamping the lead connective ends 10 within their respective receptacles 31-36. To release the lead connective ends 10 from their respective receptacles 31-36, the aforementioned process is reversed.

The preceding discussion pertains to various embodiments wherein the female fastener portion 48 includes the head 81 and is free to rotate relative to the male fastener portion 46, which is fixed to the second side clamp 44 and prevented from rotating relative to the front support portion 52. However, in other embodiments, the male fastener portion 46 includes the head and is free to rotate relative to the female fastener portion 48, which is fixed to the first side clamp 42 and prevented from rotating relative to the front support portion 52.

The preceding discussion pertains to various embodiments wherein the male fastener portion 46 includes a ring 200, the female fastener portion 48 includes an anchor 90 with a flexible flange 92, and the fastener portions 46, 48 are passed into the bore 70 of the front support portion 52 via the side of the front support portion 52 having the first side clamp 42. However, in other embodiments, the ring 200 of the male fastener portion 46 can be replaced with an anchor similar to the anchor 90 on the female fastener portion 48. With such an embodiment, the male fastener portion 46 could pass into the bore 70 of the front support portion 52 via the side of the front support portion 52 having the second side clamp 44.

As can be understood from FIGS. 2, 8 and 9, in one embodiment, the lead retention assembly 22 is advantageous for a number of reasons. For example, a physician can cause both side clamps 42, 44 to generally simultaneously clamp against the front support portion 52 by applying a tool (e.g., screw drive or wrench) to the heads 81 of the fasteners 45 on a single side of the lead retention assembly 22. In other words, each fastener 45 is coupled to both side clamps 42, 44 such that rotating the head 81 of a single fastener 45 results in generally simultaneous translation of both side clamps 42, 44 relative to the front support portion 52. Thus, connection of lead connective ends 10 to an implantable pulse generator (e.g., pacemaker, defibrillator, etc.) via the above-described lead retention assembly 22 is more efficient than other lead retention assemblies that have head equipped fasteners on each side clamp and require a physician to rotate fasteners associated with a first side clamp to cause the first side clamp to clamp before rotating fasteners associated with a second side clamp to cause the second side clamp to clamp.

Figure 12:
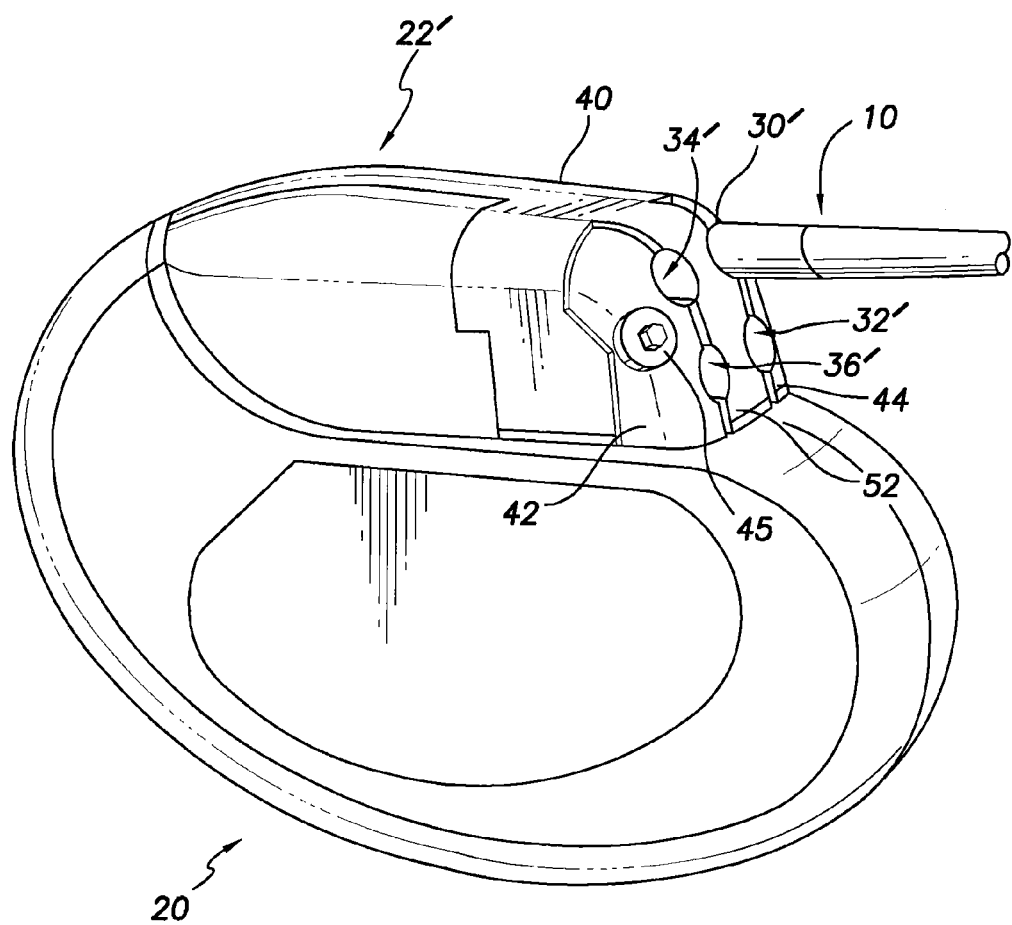
FIG. 12 is a perspective view of a cardiac pacemaker/defibrillator unit including an example of a lead retention assembly.

FIG. 12 shows an example of an implantable medical device 20 incorporating an embodiment of a lead retention assembly 22'. In this example, the lead retention assembly 22' includes four ports/receptacles 30', 32', 34', 36'. Further, the lead retention assembly 22' includes a single fastener 45. As described above, the single fastener 45 is similar to that depicted in FIGS. 9-11 and facilitates the generally simultaneous actuation of both side clamps 42, 44 to clamp lead connector ends 10 into the receptacles 30', 32', 34', 36'. In particular, the clamping action may be performed by actuating the fastener 45 from only one side such that both side clamps 42, 44 move toward the front support portion 52 generally simultaneously via rotating engagement of a head 81 of a single fastener 45. Thus, the number of fasteners needed is reduced, for example, from two to one, the number fasteners heads that need to be accessed is reduced, for example, from two to one, and the number of sides of an lead retention assembly that need to be accessed is reduced from two to one.

The mounting of the lead retention assembly 22' on the implantable medical device 20 may be in any known or hereafter developed manner, and thus is not described herein. It should be understood that any suitable location of the lead retention assembly 22' on the implantable medical device 20 may be employed, for example, depending on the particular configuration of the implantable medical device 20.

FIGS. 13-16 are generally the same views depicted in FIGS. 8-11, except of another embodiment of a lead retention assembly 122. In the embodiment depicted in FIGS. 13-16, various elements may be substantially identical to the embodiments discussed with respect to FIGS. 2-12. However, the embodiment depicted in FIGS. 13-16 differs with respect to the fastener and the bore in which the fastener is inserted. These features of the embodiment depicted in FIGS. 13-16 are discussed in detail below, with minimal detail regarding the features similar to the embodiments depicted in FIGS. 2-12.

Figure 13:
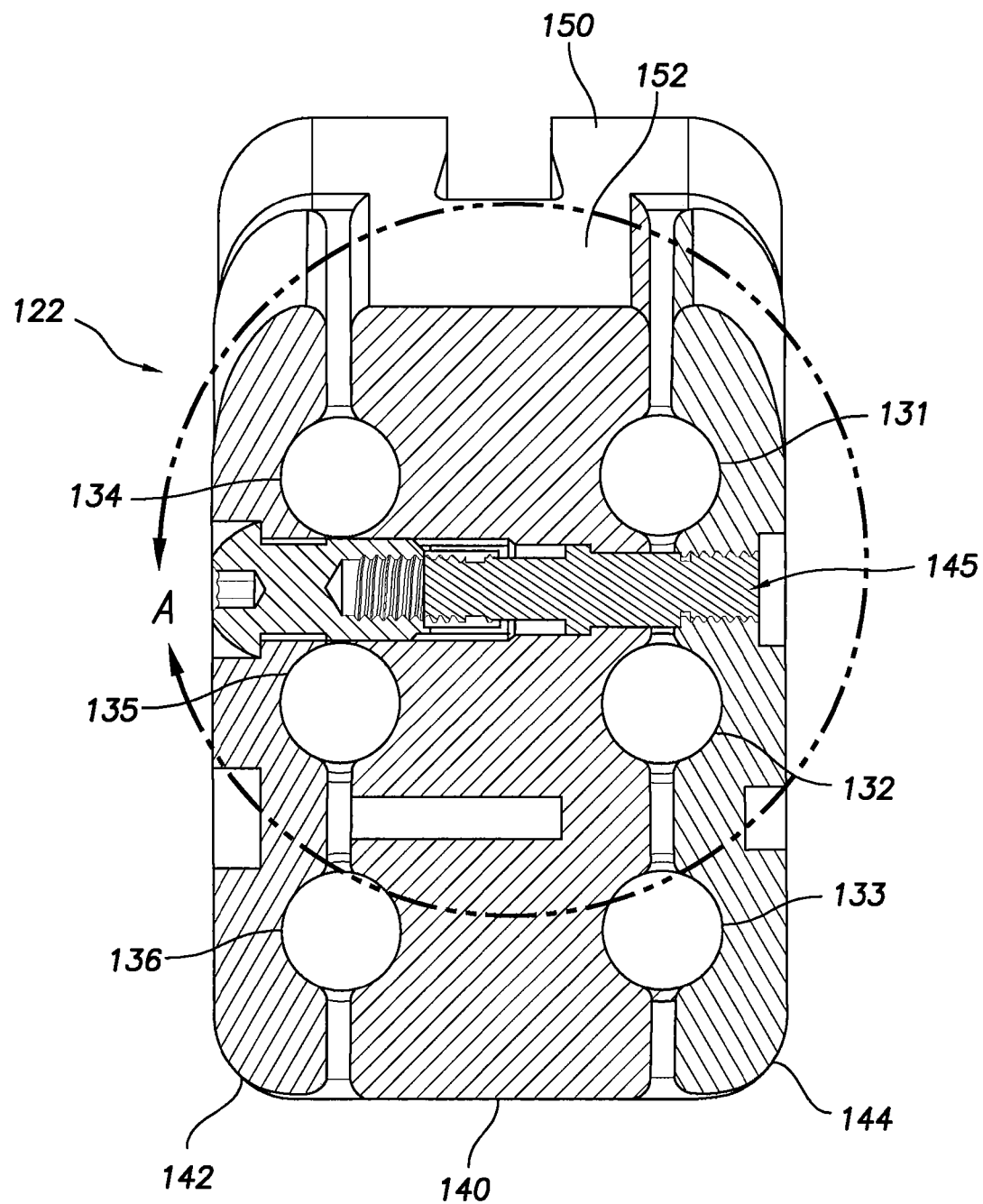
FIG. 13 is a cross sectional view of another example of a lead retention assembly, similar to FIG. 8.
Figure 15:
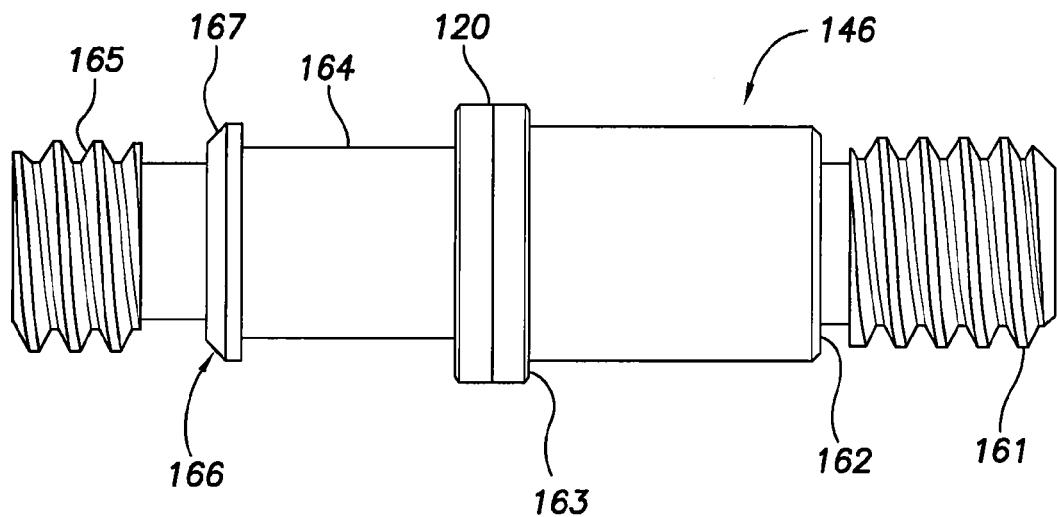
FIG. 15 is a side elevation view of one portion of the fastener of FIG. 13.

As shown in FIGS. 13 and 15, the lead retention assembly 122 may include a plurality of ports that define a first set of receptacles 131, 132, 133 and a second set of receptacles 134, 135, 136. The lead retention assembly 122 may include a support 140 with a rear support portion 150 and a front support portion 152, opposed first and second side clamps 142, 144, and one or more fasteners 145 for securing the side clamps to the front support portion 152 to clamp lead connective ends in place.

Figure 14:
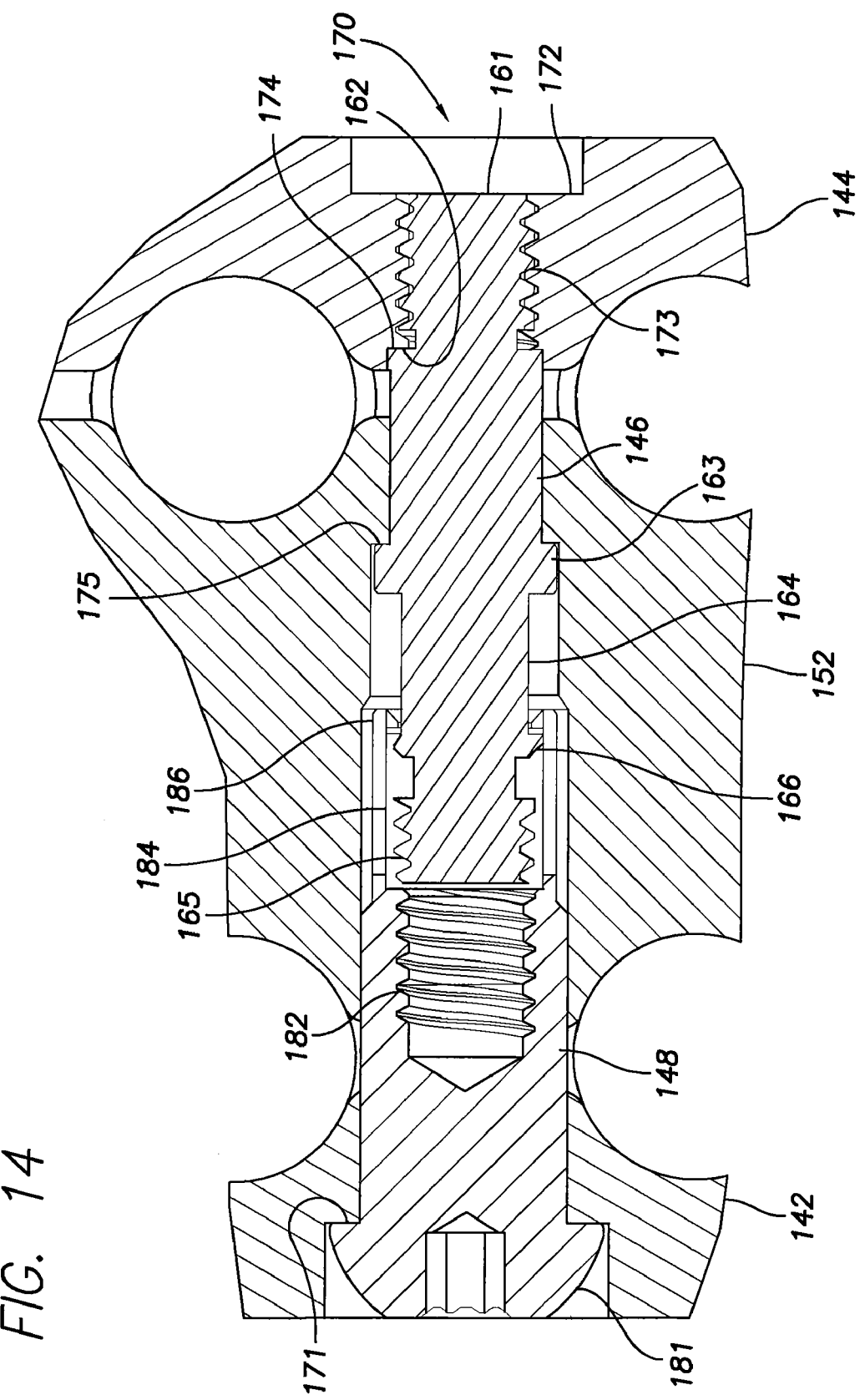
FIG. 14 is a partial enlarged view of detail A' in FIG. 13.

As shown in detail in FIGS. 13-16, a bore 170 for receiving each fastener 145 may extend through the side clamps 142, 144 and the front support portion 152 of the lead retention assembly 122. As shown in FIGS. 13 and 14, the bore 170 may provide a first outer shoulder 171 in the first side clamp 142 and a second outer shoulder 172 in the second side clamp 144.

The bore 170 may provide an internal clamp thread 173 and a first inner shoulder 174 in the second side clamp 144. The bore 170 may provide a second inner shoulder 175 in the front support portion 152. The fastener 145 may include corresponding features that cooperate with the features of the bore 170, as described below.

Figure 16:
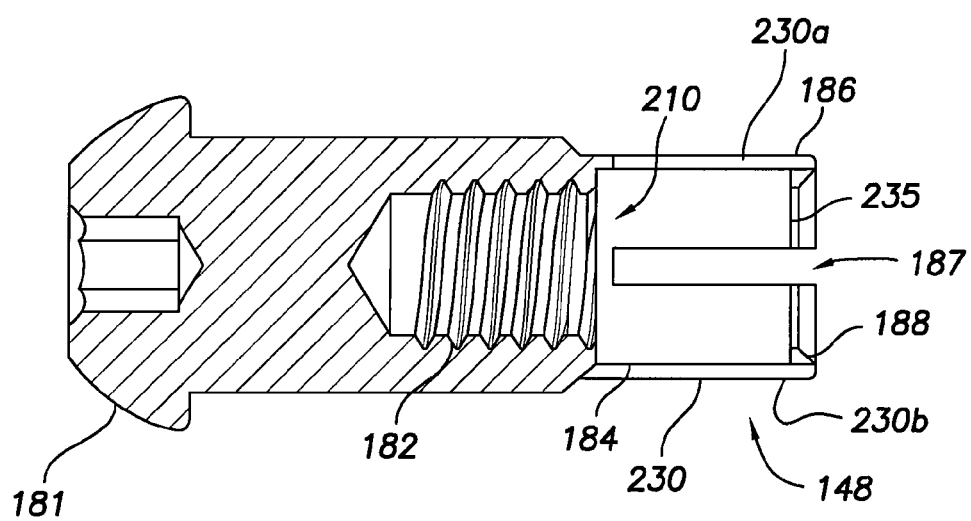
FIG. 16 is a cross-sectional view of another portion of the fastener of FIG. 13.

The fastener 145 may include a first or male fastener portion 146 and a second or female fastener portion 148. FIG. 15 shows details of the male fastener portion 146. FIG. 16 shows details of the female fastener portion 148. FIGS. 13 and 14 show the fastener portions 146, 148 engaged to render the fastener 145 operative in the lead retention assembly 122.

With reference to FIG. 15, the male fastener portion 146 may include a first threaded end 161 configured to engage the internal clamp thread 173 in the second side clamp 144. The male fastener portion 146 may include a first shoulder 162 configured to abut the first inner shoulder 174 in the second side clamp 144, for example, when the first threaded end 161 is fully engaged in the internal clamp thread 173.

The male fastener portion 146 may also include a ring 200 and a second shoulder 163 configured to abut the second inner shoulder 175 in the front support portion 152, for example, when the lead retention assembly 122 is fully opened to the maximum extent, as depicted in FIG. 13.

A narrower diameter portion 164 of the male fastener portion 146 may extend from the second ring 200 to provide a second threaded end 165. As described below, the narrower diameter portion 164 of the male fastener portion 146 may be configured to allow the second threaded end 165 to cooperate with the female fastener portion 148. In particular, the narrower diameter portion 164 of the male fastener portion 146 may include a flange 166 that extends radially outwardly. The flange 166 may include a chamfer 167.

With reference to FIGS. 14 and 16, the female fastener portion 148 may include a head 181 configured to engage the first outer shoulder 171 of the first side clamp 142, for example, when the lead retention assembly 122 is fully closed or the head 181 is driving the first side clamp 142 to the closed or clamped state.

Figure 17:
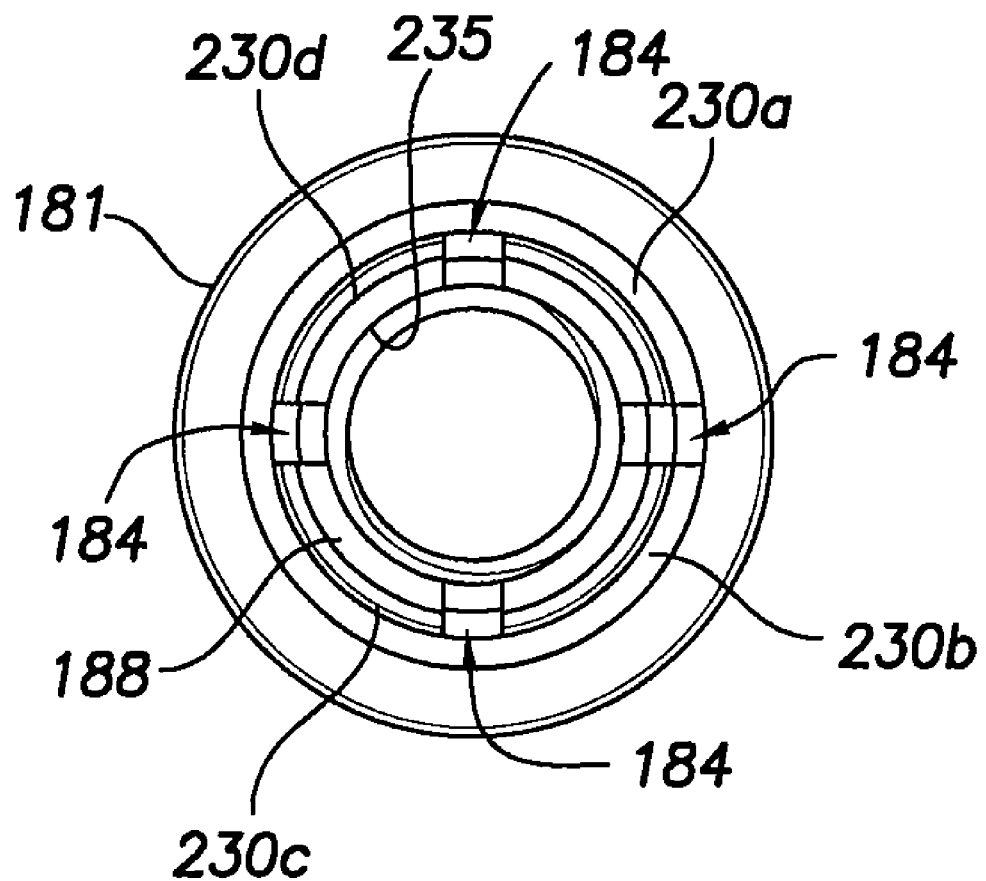
FIG. 17 is an end view of the female fastener portion, as viewed from the bore end of the female fastener portion.

As indicated in FIG. 16 and FIG. 17, which is an end view of the female fastener portion 148 as viewed from the bore end of the female fastener portion 148, the female fastener portion 148 may include a bore 210 with an internal thread 182 that is longitudinally separated from a flanged end 186 by an unthreaded portion 184. The flanged end 186 includes flanges 235. The cylindrical shaft portion 230 of the female fastener portion 148 forms unthreaded portion 184 and may include one or more longitudinal slots 187 that segments the cylindrical shaft portion 230 into two or more radial shaft segments 230a, 230b, 230c, 230d, as best understood from FIG. 17. The radially segmented configuration of the cylindrical shaft portion 230 of the female fastener portion 148 allows the flange 166 of the male fastener portion 146 to pass the flanges 235 of the flanged end 186 of the female fastener portion 148, for example, by allowing the flanged end 186 to flex outwardly. Alternatively, the flanged end 186 and/or the unthreaded portion 184 may be sufficiently flexible for such purpose and not require the radially segmented configuration of the cylindrical shaft portion 230 of the female fastener portion 148.

The flanges 235 of the flanged end 186 of the female fastener portion 148 may also include chamfers 188 that cooperate with the chamfer 167 of the flange 166 of the male fastener portion 146 to facilitate insertion of the flange 166 of the male fastener portion 146 past the flanged end 186 into the unthreaded portion 184 of the female fastener portion 148. Thus, the fastener portions 146, 148 may be secured together by pushing them longitudinally towards each other. In such a condition, the second threaded end 165 may be movable within the unthreaded portion 184, for example, to provide a limited amount of play or relative movement of the fastener portions 146, 148 while connected and, as a result, a limited amount of movement of the side clamps 142, 144 relative to the front support portion 152.

As with the embodiments discussed with respect to FIGS. 2-12, rotating the female fastener portion 148 relative to the male fastener portion 146, which, in one embodiment, is fixed to the second side clamp 144, causes the second threaded end 165 of the male fastener portion 146 to engage the first threaded portion 182 of the female fastener portion 148. Thus, the engaged threads cause the fastener portions 146, 148 to translate toward each other. Such translation causes both the first and second side clamps 142, 144 to move toward the front support portion 152 to thereby lead connective ends 10 that are inserted into the receptacles.

As can be understood from the preceding discussion, the fasteners 45 act as actuators 45 for actuating the side clamps 42, 44 to secure the leads to the pulse generator (e.g., defibrillator, pacemaker, or ICD) 20. Lead connective ends 10 are placed in their respective receptacles 31-36, and the actuators 45 are manipulated to cause both of the clamps 42, 44 connected thereto to clamp the lead connective ends between the front support portion 52 and the respective clamp. As can be understood from the preceding discussion, in one embodiment, each actuator 45 is operably coupled to both clamps 42, 44. Actuation of a single actuator 45 impacts the positional relationship of both clamps 42, 44 relative to the front support portion 52. Thus, rotating a single actuator 45 in a first direction relative to the generator 20 can cause both clamps 42, 44 to generally simultaneously increasingly clamp lead connective ends 10 against the front support portion 52. Conversely, rotating a single actuator 45 in a second direction relative to the generator 20 can cause both clamps 42, 44 to generally simultaneously decreasingly clamp lead connective ends 10 against the front support portion 52.

Although the present invention has been described with reference to particular embodiments, persons skilled in the art will recognize that changes may be made in form and detail without departing from the spirit and scope of the invention.

What is claimed is:

1. A lead retention assembly for connecting a plurality of electrical leads to an implantable medical device, the lead retention assembly comprising:
   a first receptacle having a longitudinally extending first port and a second receptacle having a second longitudinally extending second port, each receptacle including an electrical contact for electrically connecting the respective electrical lead to electrical circuitry of an implantable medical device;
   a support member having a first side recess, a second side recess, a first longitudinally bisected port with a first surface, and a second longitudinally bisected port with a second surface;
   a first side clamp having a third longitudinally bisected port with a third surface, the first side recess of the support member to receive the first side clamp such that the first surface of the support member is confrontally disposed with the third surface of the first side clamp to define the first longitudinally extending port;
   a second side clamp having a fourth longitudinally bisected port with a fourth surface, the second side recess of the support member to receive the second side clamp such that the second surface of the support member is confrontally disposed with the fourth surface of the second side clamp to define the second longitudinally extending port; and
   a fastener configured to urge both the first and second side clamps toward the support member upon actuation of the fastener and to thereby clamp the connective ends of the respective electrical lead bodies within the first and second longitudinally extending ports.

2. The lead retention assembly of claim 1, wherein the fastener comprises:
   a first portion configured to engage the first side clamp; and
   a second portion configured to engage the second side clamp;
   the first and second portions configured to be threadedly engaged with one another such that rotation of one of the first and second portions causes the first and second portions to translate toward one another.

3. The lead retention assembly of claim 2, wherein at least one of the first and second portions is retained with the support member.

4. The lead retention assembly of claim 2, wherein one of the first and second portions is configured to engage the respective first or second side clamp via a shoulder and to engage the support via an anchor.

5. The lead retention assembly of claim 4, wherein the anchor comprises a radially extending flange configured to engage a shoulder of the support member.

6. The lead retention assembly of claim 5, wherein the anchor is fixedly secured to the one of the first and second portions.

7. The lead retention assembly of claim 2, wherein one of the first and second portions is configured to engage the respective first or second side clamp via a threaded connection and to engage the support via a shoulder.

8. The lead retention assembly of claim 2, wherein one of the first and second portions comprises a first threaded section and a second threaded section separated by a threadless section.

9. The lead retention assembly of claim 2, wherein one of the first and second portions comprises a generally outwardly extending flange, the other of the first and second portions comprises a generally inwardly extending flange, and the outwardly and inwardly extending flanges are configured to engage one another to secure the first and second portions together with a limited relative movement therebetween.

10. The lead retention assembly of claim 9, wherein the inwardly extending flange includes at least one longitudinal slot that allows at least a portion of the inwardly extending flange to move outwardly.

11. The lead retention assembly of claim 9, wherein at least one of the inwardly and outwardly extending flanges includes a chamfer that facilitates movement of the flanges past one another for engagement thereof.

12. A method of connecting a plurality of electrical leads to an implantable medical device, the method comprising:

providing a lead retention assembly including a support member, a first side clamp and a second side clamp, a first port and a second port each defining a respective first receptacle and second receptacle in conjunction with the support member, and a fastener configured to urge both the first and second side clamps toward the support member upon actuation of the fastener;

wherein the support member has a first side recess, a second side recess, a first longitudinally bisected port with a first surface, and a second longitudinally bisected port with a second surface;

wherein the first side clamp has a third longitudinally bisected port with a third surface, the first side recess of the support member to receive the first side clamp such that the first surface of the support member is confrontally disposed with the third surface of the first side clamp to define the first longitudinally extending port;

wherein the second side clamp has a fourth longitudinally bisected port with a fourth surface, the second side recess of the support member to receive the second side clamp such that the second surface of the support member is confrontally disposed with the fourth surface of the second side clamp to define the second longitudinally extending port;

providing at least two electrical lead bodies each including a respective proximal end portion;

inserting the respective proximal end portions into the respective receptacles to be in electrical communication with a respective electrical contact in the respective receptacles; and actuating the fastener to thereby clamp the proximal end portions of the respective electrical lead bodies within the first and second ports.

13. The method of claim 12, wherein actuating the fastener comprises:

rotating a first portion of the fastener relative to a second portion of the fastener such that the first and second portions to translate toward one another.

14. The method of claim 13, further comprising retaining at least one of the first and second portions with the support member.

15. The method of claim 14, wherein retaining at least one of the first and second portions comprises securing an anchor to the first and/or second portions.

16. The method of claim 13, further comprising engaging at least one of the first and second portions with the respective first or second side clamp via a threaded connection.

17. The method of claim 13, further comprising connecting the first and second portions together with a limited relative movement.

\* \* \* \* \*